US009463205B2

(12) United States Patent
Berggren et al.

(10) Patent No.: US 9,463,205 B2
(45) Date of Patent: Oct. 11, 2016

(54) NON-INVASIVE IN VIVO IMAGING AND METHODS FOR TREATING TYPE I DIABETES

(71) Applicant: Biocrine AB, Solna (SE)

(72) Inventors: Per-Olof Berggren, Solna (SE); Alejandro Caicedo, Miami, FL (US)

(73) Assignee: BioCrine AB, Stockholm (SE)

( * ) Notice: Subject to any disclaimer, the term of this patent is extended or adjusted under 35 U.S.C. 154(b) by 0 days.

(21) Appl. No.: 14/515,000

(22) Filed: Oct. 15, 2014

(65) Prior Publication Data

US 2015/0064144 A1  Mar. 5, 2015

Related U.S. Application Data

(62) Division of application No. 12/199,473, filed on Aug. 27, 2008.

(60) Provisional application No. 61/042,482, filed on Apr. 4, 2008, provisional application No. 60/989,038, filed on Nov. 19, 2007, provisional application No. 60/969,437, filed on Aug. 31, 2007.

(51) Int. Cl.
*A61K 35/39* (2015.01)
*C12N 5/07* (2010.01)
*C12N 5/071* (2010.01)
*A01K 67/027* (2006.01)
*A61K 49/00* (2006.01)

(52) U.S. Cl.
CPC ........... *A61K 35/39* (2013.01); *A01K 67/0271* (2013.01); *A61K 49/0008* (2013.01); *A01K 2217/05* (2013.01); *A01K 2227/105* (2013.01); *A01K 2267/0325* (2013.01); *C12N 2830/008* (2013.01)

(58) Field of Classification Search
CPC .............................. A61K 35/39; C12N 5/0676
USPC ................................ 424/93.1, 93.7; 435/325
See application file for complete search history.

(56) References Cited

U.S. PATENT DOCUMENTS

| | | |
|---|---|---|
| 5,650,135 A | 7/1997 | Contag |
| 5,650,435 A | 7/1997 | Madara et al. |
| 7,198,774 B2 | 4/2007 | Contag et al. |
| 2004/0197792 A1 | 10/2004 | Whyte et al. |
| 2005/0180959 A1 | 8/2005 | Eulenberg et al. |

FOREIGN PATENT DOCUMENTS

| | | |
|---|---|---|
| DE | 19703734 A1 | 8/1998 |
| JP | 2004-500576 | 1/2004 |
| SU | 1369039 A1 | 9/1988 |

OTHER PUBLICATIONS

Zharkov et al. (1988) Byulleten' Eksperimental'noi Biologii i Meditsiny, vol. 105(2) 216-219, english translation.*
Hatchell et al. (1998) Transplantation Proceedings, vol. 30, 593-595.*
Myrsen et al. (1996) Diabetologia, vol. 39, 54-59.*
Philipson et al. (2004), "Imaging Metabolic and Signaling Targets in the Pancreatic Beta Cell." Curr. Med. Chem.—Immun., Endoc.& Metab. Agents 4: 333-337.
Porksen et al. (1994), "Coordinate pulsatile insulin secretion by chronic intraportally transplanted islets in the isolated perfused rat liver." J. Clin. Invest. 94: 219-27.
Rahier et al. (1983), "Cellular composition of the human diabetic pancreas." Diabetologia 24: 366-71.
Saiardi et al. (2001), "GRAB: a physiologic guanine nucleotide exchange factor for Rab3A, which interacts with inositol hexakisphosphate kinase." Neuron 31(3): 439-51.
Saiardi et al. (2001), "Identification and characterization of a novel inositol hexakisphosphate kinase." J. Biol. Chem. 276(42): 39179-85.
Saiardi et al. (2004), "Phosphorylation of proteins by inositol pyrophosphates." Science 306: 2101-5.
Shapiro et al. (2000), "Islet transplantation in seven patients with type 1 diabetes mellitus using a glucocorticoid-free immunosuppressive regimen." N. Engl. J. Med. 343: 230-8.
Speier et al. (2003), "A novel approach to in situ characterization of pancreatic beta-cells." Pflugers Arch. 446: 553-8.
Speier et al. (2008), "Noninvasive in vivo imaging of pancreatic islet cell biology." Nat. Med. 14(5): 574-8.
Speier et al. (2008), "Noninvasive high-resolution in vivo imaging of cell biology in the anterior chamber of the mouse eye." Nat. Protoc. 3(8): 1278-86.
Szkudelski (2001), "The mechanism of alloxan and streptozotocin action in B cells of the rat pancreas." Physiol. Res. 50: 537-46.
Tret'Yak et al. (1989), "The compensation of experimental diabetes in rats by means of the transplantation of embryonal pancreatic gland into the anterior chamber of the eye." Translated from Doklady Akademii Nauk SSSR 304 (2): 506-8.
Trubetskaya et al. (1994), "DNA hyperproduction in the blood plasma of animals with experimental diabetes and its compensation using the transplantation of insulin-producing tissue into the anterior chamber." Izvestia Akademii Nauk. Seriia Biologicheskaia (1): 152-5, English abstract.
Valdeolmillos et al. (1989), "Glucose-induced oscillations of intracellular Ca2+ concentration resembling bursting electrical activity in single mouse islets of Langerhans." FEBS Lett. 259: 19-23.
Vetterlein et al. (1986), "Distribution of capillary blood flow in rat kidney during postischemic renal failure." Am. J. Physiol. 251: H510-9.
Vetterlein et al. (1987), "Morphometric investigation of the microvascular system of pancreatic exocrine and endocrine tissue in the rat." Microvasc. Res. 34: 231-8.
Wajchenberg (2007), "Beta-Cell Failure in Diabetes and Preservation by Clinical Treatment." Endocr Rev. 28(2): 187-218.
Wenna, N. D. (2007), "Serum proteins in Type 1 diabetes." Thesis from the Rolf Luft Research Center for Diabetes and Endocrinology, Department of Molecular Medicine and Surgery, Karolinska Institutet, Stockholm, Sweden.

(Continued)

*Primary Examiner* — Anne Marie S Wehbe
(74) *Attorney, Agent, or Firm* — McDonnell Boehnen Hulbert & Berghoff LLP

(57) ABSTRACT

The present invention provides novel drug discovery platforms and methods for treating type I diabetes.

6 Claims, 5 Drawing Sheets

(56) References Cited

OTHER PUBLICATIONS

Woods et al. (1974), "Neural control of the endocrine pancreas." Physiol. Rev. 54: 596-619.

Wu et al. (1993), "Transplantation of the mammalian pineal gland: studies of survival, revascularization, reinnervation, and recovery of function." Experimental Neurology 122: 88-99.

Zambre et al. (1999), "Inhibition of human pancreatic islet insulin release by receptor-selective somatostatin analogs directed to somatostatin receptor subtype 5." Biochem. Pharmacol. 57: 1159-1164.

Zharkov et al. (1988), "Implantation of embryonic pancreas in the anterior chamber of the eye in normal and diabetic rats." Translated from Byulleten' Eksperimental'noi Biologii I Meditsiny 105(2): 216-219.

Zharkov et al. (1989), "Development and function of embryonic pancreatic islet cells in the anterior chamber of the rat eye." Translated from Byulleten' Eksperimental'noi Biologii I Meditsiny 107(3): 342-345.

Zhuravleva et al. (1984), "Organization of the nervous tissue (hippocampus and septum) developing in the anterior eye chamber. I. General characteristic and non-neural elements." Journal fur Hirnforschung 25: 313-330.

Grisanti, et al. (2002) Japanese Journal of Ophthalmology, 46(1): 36-44, abstract.

Kullander (1959) Acta Endocrinologica, 31(1): 123-129, abstract.

Grimelius et al., "Studies on islet tissue transplants in the anterior chamber of the eye in rats" Wenner Gren Center Int. Symp. (1964), vol. 3, pp. 173-178.

Nyqvist Thesis "In vivo imaging of islet cells and islet revascularization" Karolinska Institute, Stockholm, Sweden (2007).

Urtti (2006) Adv. Drug Deliv. Rev., vol. 58, pp. 1131-1135.

Shitara et al. (2001) FEBS lett., vol. 500(1-2), pp. 7-11.

Adeghate (2002) Transplant Immunology, vol. 10, pp. 73-80.

Adeghate et al. (1990), "Distribution of neuropeptide Y and vasoactive intestinal polypeptide immunoreactive nerves in normal and transplanted pancreatic tissue." Peptides 11: 1087-1092.

Adeghate et al. (1990), "Morphological findings in long-term pancreatic tissue transplants in the anterior eye chamber of rats." Pancreas 5: 298-305.

Adeghate (1998), "Host-graft circulation and vascular morphology in pancreatic tissue transplants in rats." The Anatomical Record 251: 448-459.

Adeghate et al. (2001), "Comparative morphology and biochemistry of pancreatic tissue fragments transplanted into the anterior eye chamber and subcutaneous regions of the rat." European Journal of Morphology 39: 257-268.

Adeghate (2002), "Pancreatic tissue grafts are reinnervated by neuro-peptidergic and cholinergic nerves within five days of transplantation." Transplant Immunology 10: 73-80.

Arbuzova et al. (1991), "Levels of immunoreactive insulin in the pancreas and allograft to the anterior chamber of the eye in experimental diabetes." Problemy Endokrinologii 37(1): 42-4, English abstract.

Aynsley-Green et al. (1973), "Anaesthesia and insulin secretion: the effects of diethyl ether, halothane, pentobarbitone sodium and ketamine hydrochloride on intravenous glucose tolerance and insulin secretion in the rat." Diabetologia 9: 274-281.

Barker et al. (2002), "Phosphorylated inositol compounds in B-cell stimulus-response coupling." Am. J. Physiol. Endocrinol. Metab. 283: E1113-1122.

Berggren et al. (2006), "Novel aspects on signal-transduction in the pancreatic beta-cell." Nutr Metab Cardiovasc Dis 16 Suppl 1: S7-10.

Bernd et al. (2004), "Influence of molecular weight on intracameral dextran movement to the posterior segment of the mouse eye." Investigative Ophthalmology & Visual Science 45: 480-484.

Berney et al. (2001), "Endotoxin-mediated delayed islet graft function is associated with increased intra-islet cytokine production and islet cell apoptosis." Transplantation 71: 125-132.

Bhandari et al. (2008), "Gene deletion of inositol hexakisphosphate kinase 1 reveal inositol pyrophosphate regulation of insulin secretion, growth and spermiogenesis." Proc. Natl. Acad. Sci. USA 105(7): 2349-53.

Boersma et al. (2005), "Past, present, and future of annexin A5: from protein discovery to clinical applications." J. Nucl. Med. 46: 2035-50.

Boutet De Monvel et al. (2001), "Image restoration for confocal microscopy: improving the limits of deconvolution, with application to the visualization of the mammalian hearing organ." Biophysical Journal 80: 2455-2470.

Brown et al. (2005), "Anesthesia can cause sustained hyperglycemia in C57/BL6J mice." Visual Neuroscience 22: 615-618.

Butler et al. (2003), "Beta-cell deficit and increased beta-cell apoptosis in humans with type 2 diabetes." Diabetes 52: 102-10.

Cejvan et al. (2003), "Intra-islet somatostatin regulates glucagon release via type 2 somatostatin receptors in rats." Diabetes 52: 1176-1181.

Chakrabarti et al. (2003), "Ragaglitazar: a novel PPAR-alpha & PPAR-gamma agonist with potent lipid-lowering and insulin-sensitizing efficacy in animal models." Br. J. Pharmacology 140: 527-37.

Communication Relating to the Results of the Partial International Search for PCT Application No. PCT/EP2008/007130, mailed Dec. 15, 2008.

Dekki et al. (2007), "Type 1 diabetic serum interferes with pancreatic beta-cell Ca2+-handling." Biosci. Rep. 27: 321-6.

Desborough et al. (1993), "Isoflurane inhibits insulin secretion from isolated rat pancreatic islets of Langerhans." British Journal of Anaesthesia 71: 873-876.

Fagan et al. (1998), "Insulin secretion is inhibited by subtype five somatostatin receptor in the mouse." Surgery 124:254-8.

Hatchell et al. (1998), "Transplantation of feline islets of Langerhans in the subretinal space of cat eyes." Transplantation Proceedings 30: 593-5.

Hoffer et al. (1974), "Electrophysiological and cytological studies of brain homografts in the anterior chamber of the eye: maturation of cerebellar cortex in oculo." Brain Research 79: 165-184.

Hokanson et al. (2006), "Susceptibility to type 1 diabetes is associated with ApoCIII gene haplotypes." Diabetes 55: 834-8.

Hultquist (1972), "The ultrastructure of pancreatic tissue from duct-ligated rats implanted into anterior chamber of rat eyes." Ups. J. Med. Sci. 77: 8-18.

International Search Report for PCT Application No. PCT/EP2008/007130, mailed Jun. 17, 2009.

Junti-Berggren et al. (2004), "Apolipoprotein CIII promotes Ca2+-dependent beta cell death in type 1 diabetes." Proc. Natl. Acad. Sci. USA 101(27): 10090-4.

Kamimura et al. (2004), "The IHPK1 gene is disrupted at the 3p21.31 breakpoint of t(3;9) in a family with type 2 diabetes mellitus." J. Hum. Genet. 49: 360-5.

Katoh et al. (1991), "Target-specific innervation by autonomic and sensory nerve fibers in hairy fetal skin transplanted into the anterior eye chamber of adult rat." Cell and Tissue Research 266: 259-263.

Klein et al. (2004), "Apolipoprotein C-III protein concentrations and gene polymorphisms in type 1 diabetes: associations with lipoprotein subclasses." Metabolism 53(10): 1296-304.

Klein et al. (2005), "Apolipoprotein C-III protein concentrations and gene polymorphisms in Type 1 diabetes: associations with microvascular disease complications in the DCCT/EDIC cohort." J. Diabetes. Complications 19(1): 18-25.

Köhler et al. (2003), "On-line monitoring of apoptosis in insulin-secreting cells." Diabetes 52: 2943-50.

Köhler et al. (2004), "Imaging of Pancreatic Beta-Cell Signal-Transduction." Curr. Med. Chem.—Immun., Endoc.& Metab. Agents 4: 281-299.

Koo et al. (2006), "Non-invasive in vivo imaging in small animal research." Cell Oncol. 28: 127-139.

Kulikov et al. (1998), "Tissue transplantation as a compensation for deleterious effects of ageing, radiation, diabetes, and craniocerebral trauma." Membrane Cell Biology 11(6): 737-42.

(56) References Cited

OTHER PUBLICATIONS

Lai et al. (1999), "Tracking RPE transplants labeled by retroviral gene transfer with green fluorescent protein." Investigative Ophthalmology and Visual Science 40(9): 2141-6.

Lipp et al. (1993), "Ratiometric confocal Ca(2+)-measurements with visible wavelength indicators in isolated cardiac myocytes." Cell Calcium 14: 359-72.

Mathis et al. (2001), "Beta-Cell death during progression to diabetes." Nature 414: 792-8.

Medarova et al. (2005), "Imaging beta-cell death with a near-infrared probe." Diabetes 54: 1780-8.

Meier et al. (2006), "Intrahepatic transplanted islets in humans secrete insulin in a coordinate pulsatile manner directly into the liver." Diabetes 55: 2324-32.

Menger et al. (1992), "Influence of experimental hyperglycemia on microvascular blood perfusion of pancreatic islet isografts." J. Clin. Invest. 90: 1361-9.

Menger et al. (2001), "Revascularization and microcirculation of freely grafted islets of Langerhans." World J. Surg. 25: 509-15.

Nagamatsu et al. (2007), "IP7 debut in insulin release." Science 318: 1249-50.

Niederkorn (2002), "Immune privilege in the anterior chamber of the eye." Critical Reviews in Immunology 22: 13-46.

Nyqvist et al. (2005), "Pancreatic islet function in a transgenic mouse expressing fluorescent protein." J. Endocrinology 186: 333-341.

Nyqvist et al. (2005), "Donor islet endothelial cells participate in formation of functional vessels within pancreatic islet grafts." Diabetes 54: 2287-93.

Nyqvist, Daniel (2007), "In vivo imaging of islet cells and islet revascularization." Thesis from the Rolf Luft Research Center for Diabetes and Endocrinology, Department of Molecular Medicine and Surgery, Karolinska Institutet, Stockholm, Sweden.

Olson et al. (1976), "Beating intraocular hearts: light-controlled rate by autonomic innervation from host iris." Journal of Neurobiology 7: 193-203.

Paty et al. (2004), "Toward development of imaging modalities for islets after transplantation: insights from the National Institutes of Health Workshop on Beta Cell Imaging." Transplantation 77: 1133-7.

\* cited by examiner

NON-INVASIVE IN VIVO IMAGING AND METHODS FOR TREATING TYPE I DIABETES

CROSS REFERENCE

This application is a divisional of U.S. application Ser. No. 12/199,473 filed Aug. 27, 2008, which claims priority to U.S. Provisional Patent Application Ser. Nos. 60/969,437 filed Aug. 31, 2007, 61/042,482 filed Apr. 4, 2008, and 60/989,038 filed Nov. 19, 2007, all incorporated by reference herein in their entirety.

STATEMENT OF GOVERNMENT SUPPORT

The work disclosed herein was supported in part by National Institute of Health Grant Numbers DK-58508 and DK-075487 and thus the U.S. government has certain rights in the invention.

BACKGROUND OF THE INVENTION

Fundamental understanding of cellular processes in health and disease has been gained by studying cells of various tissues in vitro. However, results obtained from experiments in vitro are often not sufficient to explain the performance of cells in more physiological settings like whole organs or living organisms. To place observations made in an in vitro system into a physiological context, studies have to be performed under in vivo conditions. In recent years an increasing number of approaches have been made to investigate cell function in situ utilizing imaging techniques. Unfortunately, non-invasive imaging techniques like computer tomography (CT), magnet resonance imaging (MRI), positron emission tomography (PET) or bioluminescence imaging (BLI) lack cellular resolution[1]. On the other hand, confocal and two-photon laser-scanning microscopy (LSM) provide sub-cellular resolution but have a fairly limited working distance and imaging depth[2]. Accessing target cells for the application of LSM is mostly invasive and often excludes the possibility of repetitive examinations.

SUMMARY OF THE INVENTION

The present invention provides methods for drug development comprising:

(a) engrafting target cells into the eye of a test animal, wherein one or more cellular component of therapeutic interest in the transplanted target cells are fluorescently labeled;

(b) contacting the target cells with one or more test compounds; and (c) performing non-invasive fluorescent imaging on the eye of the test animal, wherein the fluorescent imaging is used to detect test compound-induced changes in one or more of activity, location, and amount of the fluorescently labeled cellular components of therapeutic interest in the engrafted target cells, wherein the changes identify those test compounds that may provide a therapeutic benefit to the target cells.

In another aspect, the present invention provides methods for treating a subject with type I diabetes, comprising transplanting into the eye of a subject with type I diabetes an amount effective of an insulin-producing cell to promote insulin production in the subject.

DETAILED DESCRIPTION OF THE INVENTION

Figure 1:
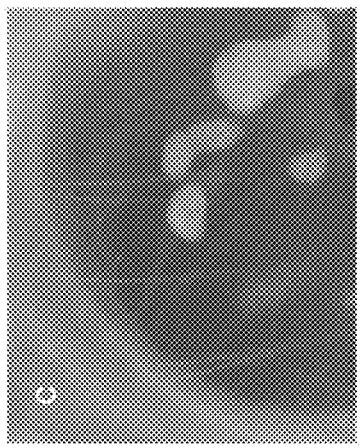
FIG. 1. Pancreatic islets transplanted into the anterior chamber of the eye. (a) Islet transplantation into the anterior chamber of the eye. (b) Set up for non-invasive in vivo imaging. (c) Digital photograph of islets engrafted on the iris in the anterior chamber of the eye. (d-g) Eye sections containing islet grafts showing insulin-immunoreactive β-cells (red) and glucagonimmunoreactive β-cells (green) at different time-points after transplantation. (h) The ratio of insulin to glucagon immunoreactive cells in islets in the pancreas and in the anterior chamber of the eye at indicated time-points after transplantation. (i) Plasma glucose levels during an intraperitoneal glucose tolerance test in streptozotocin-treated mice transplanted with islets into the eye (n=8, black) and under the kidney capsule (n=2, red).
Figure 1:
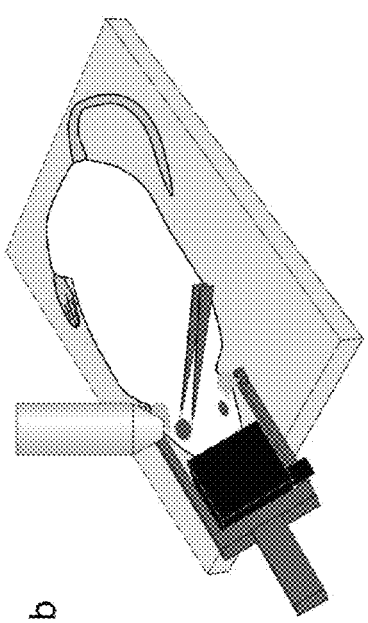
Figure 1:
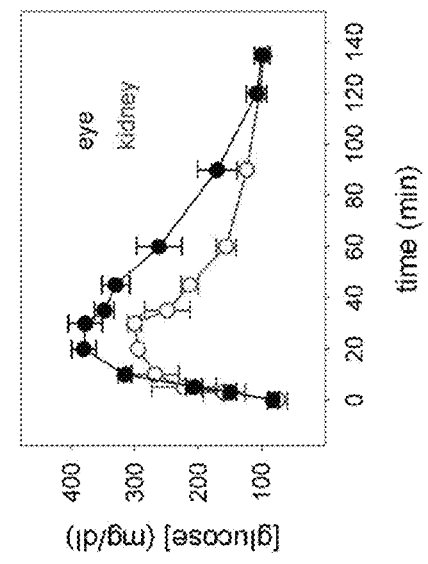
Figure 1:
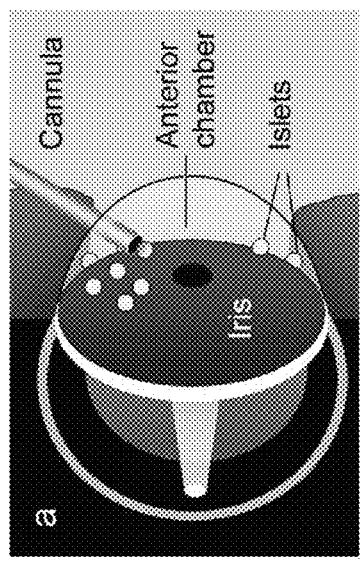
Figure 1:
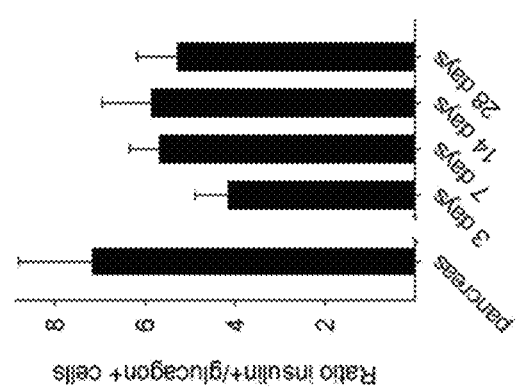
Figure 1:
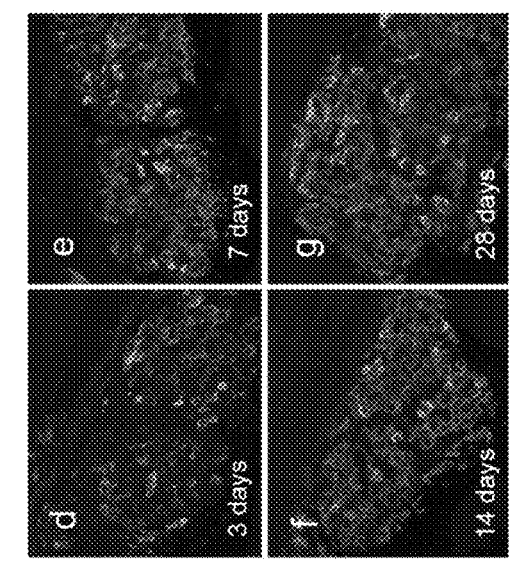

In one aspect, the present invention provides methods for drug development comprising:

(a) engrafting target cells into the eye of a test animal, wherein one or more cellular component of therapeutic interest in the transplanted target cells are fluorescently labeled;

(b) contacting the target cells with one or more test compounds; and (c) performing non-invasive fluorescent imaging on the eye of the test animal, wherein the fluorescent imaging is used to detect test compound-induced changes in one or more of activity, location, and amount of the fluorescently labeled cellular components of therapeutic interest in the engrafted target cells, wherein the changes identify those test compounds that may provide a therapeutic benefit to the target cells.

As used herein, the target cells to be transplanted may be individual cells, a plurality of cells of the same type, or a plurality of different cell types, such as tissues/tissue portions. The cells may be of any type desired to be assessed, including but not limited to endocrine cells (including but not limited to pancreatic beta cells), and cells derived from any tissue type, including but not limited to fat, muscle, brain, liver, kidney, heart, and lungs.

The methods of the invention provide a novel platform for non-invasive in vivo drug development studies that take into account the physiology and pathophysiology of any cell or tissue. In one embodiment, the anterior chamber of the eye can be used as a versatile natural body window to clarify, for the first time, the integration of complex signaling networks at the cellular level under in vivo conditions. Employing the anterior chamber of the eye as an in vivo model for assessing activity of one or more cellular components enables the continuous monitoring of, for example, morphology, vascularization, innervation, cell death, cell proliferation, cell development (including but not limited to stem cell development, tumor cell development, etc.), gene expression and cell signaling. The use of this platform can be used, for example, to elucidate the effects of modulatory inputs from, for example, the hormonal and neuronal system, as well as from autocrine/paracrine signals of endocrine or vascular cells. Furthermore, it serves as a novel approach for non-invasive in vivo studies of cell/tissue function and survival under healthy and non-healthy conditions. Thus, the model system is ideal for use, for example, in drug discovery and testing of drug candidates (including but mot limited to drug candidates for treating cancer, diabetes, etc.) in vivo.

The test mammal can be any suitable test mammal in which cells can be transplanted into the anterior chamber of the eye, including but not limited to mice, monkeys, rabbits, dogs, rats, and pigs.

The anterior chamber of the eye comprises the front portion of the eye, and includes the structure in front of the vitreous humour, as well as the cornea, iris, ciliary body, and lens. Transplantation of target cells into the anterior chamber of the eye can comprise placement of the cells into any one or more of these anterior eye chamber compartments, so long as the target cells can be observed and fluorescent signals from the cells can be non-invasively visualized. In one non-limiting example, target cells are transplanted via injection through the cornea, allowing engraftment of the transplanted target cells onto the iris, permitting observation and imaging through the cornea.

The one or more cellular components of interest in the transplanted test cells are fluorescently labeled. The labeling may be direct (ie: covalent interaction) or indirect (non-covalent interaction) cells may be labeled before or after transplantation. Pre-transplantation labeling can be accomplished by any means known in the art, including but not limited to recombinant DNA techniques, such as transfection of the cells with an expression construct that will express a fluorescent protein-labeled cellular component of interest. Any fluorescent protein can be used including but not limited to green fluorescent protein and all of its variants. Post-transplantation labeling can also be by any means known to those of skill in the art, including but not limited to injection of fluorescent stains of interest and contact with labeled antibodies.

Fluorescence imaging on the anterior eye chamber can be accomplished by any technique known to those of skill in the art, including but not limited to laser scanning microscopy. In one embodiment, the methods involve stimulating fluorescence from the labeled cellular components of interest by laser stimulation at appropriate wavelength(s) to non-invasively obtain fluorescence images of the cellular components in the transplanted cells.

The activity of any cellular component of interest can be assessed via the methods of the present invention. Such activity can be any characteristic of the cellular component of interest that can be assessed based on detection of fluorescent signals from the cellular component of interest, including but not limited to expression, distribution, localization, amount, kinetics/dynamic changes, modifications, and oscillations. In a further embodiment, the methods comprise assessing activity of the cellular component of interest over time. In this embodiment, the methods comprise performing fluorescent imaging at multiple time points, and changes in activity of the cellular component of interest can be assessed. In an embodiment of all of the embodiments herein, the assessment is done within individual cells.

In one non-limiting embodiment, the cellular component of interest comprises a component of a signal transduction pathway, and the methods comprise assessing activity of the signal transduction pathway by assessing activity of the one or more cellular components of interest over time. In a further non-limiting embodiment, the test cells comprise pancreatic beta cells.

The methods comprise contacting the target cells with one or more test compounds and assessing the activity of the fluorescently labeled cellular components of interest in the target cells in response to the one or more test compounds. Such contacting of the transplanted cells with the one or more test compounds can be pre or post-transplantation; preferably post-transplantation.

In the examples below, we transplanted isolated pancreatic islets of Langerhans into the anterior chamber of the eye. Islets of Langerhans are composed of several different cell types, including alpha-, beta- and delta-cells. These clusters of cells represent the endocrine pancreas and are of major importance for glucose homeostasis. Insufficient release of insulin from beta-cells in response to elevated blood glucose levels, leads to diabetes. The regulation of glucose induced insulin secretion from beta-cells is a complex process, modulated by autocrine, paracrine, hormonal and neuronal factors. Therefore, studies on vascularized and innervated islets of Langerhans are necessary to understand the mechanisms leading to hormone secretion in health and disease. However, due to the scattered distribution of islets of Langerhans throughout the exocrine pancreas and the anatomy of the rodent pancreas in particular, non-invasive longitudinal in vivo studies of the islets of Langerhans at single-cell resolution are currently not feasible.

We show below, that after transplantation to the anterior chamber of the eye, isolated islets readily engrafted. Diabetic mice could be rendered normoglycemic by transplanting islets of Langerhans to the anterior chamber of the eye and these mice showed identical responses to glucose tolerance tests compared to control mice. We were able to longitudinally monitor morphology of the islets and follow the revascularization process. We could also repetitively measure systemically induced changes in cytoplasmic free $Ca^{2+}$ concentration in beta-cells of the same islet. Finally, we non-invasively monitor chemically induced cell death in islets after systemic injection of a beta-cell toxin.

This platform enables non-invasive assessment of multiple morphological and functional parameters in vascularized and innervated tissue. Although the examples focus on pancreatic islets of Langerhans the introduced platform can be used to investigate all kinds of tissues. Different types of tissues, transplanted to the anterior chamber of the eye, have been shown to attract vessels and nerves and establish organotypic vascularization[10,12] and innervation[4,5,13]. This allows studying tissues in a setting comparable to their natural surrounding without having to access the tissue in an invasive manner. Furthermore, due to the characteristics of the eye, the target cells and their regulatory input can be modulated not only systemically but also locally without difficulty. Substances can be applied topically onto the eye or injected into the anterior chamber. Additionally, perfusion of the anterior chamber repetitively allows exchange of the aqueous humor or loading of the graft with fluorescent indicators.

When utilizing the anterior chamber of the eye as a transplantation site, the special local features expressed to optimize visualization and to make the anterior chamber an immune privileged site are taken into consideration. Differences in the composition of the aqueous humor inside the anterior chamber and the blood plasma are kept in mind when interpreting observations made in the anterior chamber. However, our studies have shown no obvious effects on normal graft function by the local environment. One possible explanation might be that the induced neovascularization leads to an adjustment of aqueous humor and blood plasma composition. Thus, we have demonstrated that the anterior chamber of the eye enables studies of complex biological interactions in an in vivo system at single-cell resolution. Its current form is further extendible and implementation of newly developed fluorescent proteins, biosensors and transgenic animals will help to investigate numerous parameters important for development, function and survival under both physiological and pathophysiological conditions.

In another aspect, the present invention provides methods for treating a subject with type I diabetes, comprising transplanting into the eye of a subject with type I diabetes an amount effective of an insulin-producing cell to promote insulin production in the subject.

As used in this aspect, an "insulin-producing cell" is any cell type that is capable of producing insulin after transplantation into a subject's eye. Such insulin-producing cells include, but are not limited to, pancreatic β cells, stem cells, and recombinant cells engineered to release insulin.

As used herein, "pancreatic β cells" are any population of cells that contains pancreatic β islet cells. Such pancreatic β islet cell populations include the pancreas, isolated pancreatic islets of Langerhans ("pancreatic islets") and isolated pancreatic β islet cells. Methods for pancreatic isolation are well known in the art, and methods for isolating pancreatic islets, can be found, for example, in Cejvan et al., Diabetes 52:1176-1181 (2003); Zambre et al., Biochem. Pharmacol. 57:1159-1164 (1999), and Fagan et al., Surgery 124:254-259 (1998), and references cited therein. Once implanted in the host eye, the beta cells in these islets begin to make and release insulin As disclosed herein, the inventors have disclosed a new method for monitoring real-time events in cells such as pancreatic β cells by transplanting cells into the anterior chamber of the eye. In conducting these studies, the inventors have determined that transplantation of pancreatic β cells into the eye has not led to any serious complication, such as vision loss or excessive eye irritation. Thus, given that the eye provides a somewhat immunopriviliged compartment, it is believed that transplantation of insulin-producing cells into the eye of patients with type I diabetes can provide the necessary insulin production, while allowing a lowered dosage of immunosuppressant drugs to be used, reducing the potentially severe side effects of immunosuppression. It is also believed that transplantation into the eye will reduce any period of anoxia during transplantation, resulting in an increased survival of the transplanted cells.

Transplantation into the eye preferably involves transplantation into the anterior chamber of the eye. The anterior chamber of the eye comprises the front portion of the eye, and includes the structure in front of the vitreous humour, as well as the cornea, iris, ciliary body, and lens. Transplantation of the insulin-producing cells into the anterior chamber of the eye can comprise placement of the cells into any one or more of these anterior eye chamber compartments. In one non-limiting example, test cells are transplanted via injection through the cornea, allowing engraftment of the transplanted cells onto the iris, permitting observation and imaging through the cornea. Insulin producing cells, such as pancreatic beta islets, transplanted into the anterior chamber of the eye engrafted on the iris, became vascularized, retain their cellular composition, and respond to stimulation. Furthermore, they can be monitored by non-invasive laser scanning microscopy (LSM) allowed in vivo imaging of islet vascularization, as well as beta-cell function and insulin release. In these embodiments, the insulin-producing cells or components thereof can be fluorescently labeled, and fluorescence imaging can be used to monitor cell activity.

Fluorescence imaging on the anterior eye chamber can be accomplished by any technique known to those of skill in the art, including but not limited to laser scanning microscopy. In one embodiment, the methods involve stimulating fluorescence from the labeled cellular components of interest by laser stimulation at appropriate wavelength(s) to non-invasively obtain fluorescence images of the cellular components in the transplanted cells.

EXAMPLE 1

Impaired insulin release and thereby defect glucose homeostasis in the body is a hallmark of diabetes (1). Under physiological conditions, insulin release from the pancreatic β-cell is regulated by the complex and concerted actions of cell metabolic activity, autocrine/paracrine signalling, and continuous input from hormones and neurotransmitters (2). The β-cells, together with other endocrine cell types, are situated within the endocrine pancreas, the islets of Langerhans, which are densely vascularised (3) and abundantly innervated (4). Therefore, to fully understand the complexity of β-cell signal-transduction and the mechanisms controlling insulin release in health and disease, studies need to be conducted in vascularised and innervated islets in vivo. Here, we introduce a novel noninvasive technical platform for in vivo fluorescence imaging of pancreatic islets transplanted into the anterior chamber of the mouse eye. Islets transplanted into the anterior chamber of the eye engrafted on the iris, became vascularised, retained cellular composition and responded to stimulation. Non-invasive laserscanning microscopy (LSM) allowed in vivo imaging of islet vascularization, as well as β-cell function and death. Our results thus establish the basis for repetitive non-invasive in vivo investigations of β-cell signal-transduction, which can be performed longitudinally under both normal and diabetic conditions.

Methods and Materials

Mouse models. C57BL6 and Tie2-GFP mice (STOCK Tg(TIE2GFP)287Sato/J) were purchased from the Jackson Laboratories (Bar Harbor, Me.). RIP-GFP mice were generated at a core-facility at Karolinska Institutet and were characterized by a normal glucose tolerance and β-cell restricted expression of GFP (see Methods). All experiments were approved by the local animal ethics committees at Karolinska Institutet and the University of Miami.

Transplantation of pancreatic islets to the anterior chamber of the eye. Pancreatic islets were isolated and cultured as described (25). Thirty to three hundred islets were transferred from culture media to sterile PBS and aspirated into a 27 G eye cannula connected to a 1 ml Hamilton syringe (Hamilton, Reno, Nev.) via a 0.4 mm polythene tubing (Portex Limited, Kent, England). Mice were anesthetized using isoflurane (Isoflurane, Abott Scandinavia AB, Solna, Sweden) and 0.1 ml/kg of Temgesic (Schering-Plough, NJ) was subcutaneously injected to relieve post-operative pain. Under a stereomicroscope, the cornea was punctured close to the sclera at the bottom part of the eye with a 27 G needle. Great care was taken not to damage the iris and to avoid bleeding. Next, the blunt eye cannula was gently inserted and the islets were slowly injected into the anterior chamber where they settled on the iris. After injection, the cannula was carefully withdrawn and the animal was left lying on the side before awakening. The mice quickly recovered and showed no signs of stress or irritation from the transplanted eye.

Intravital imaging of islets transplanted to the anterior chamber of the eye.

Previously transplanted mice were anesthetized with a 40% oxygen and ~2% isoflurane (Isoflurane) mixture, placed on a heating pad. The mouse head was restrained with a stereotaxic headholder (SG-4N, Narishige, Tokyo, Japan) and positioned with the eye containing the engrafted islets facing up. The eyelid was carefully pulled back and the eye was gently held at the corneoscleral junction with a pair of tweezers attached to a UST-2 Solid Universal Joint (Narishige). The tips of the tweezers were covered with a single piece of polythene tubing creating a loop between the two tips. This arrangement permitted a flexible but stable fixation of the head and eye without causing damage or disrupting the blood circulation in the eye. An upright Leica DMLFSA microscope, equipped with a TCS-SP2-AOBS confocal scanner and lasers for two-photon excitation25, was used for imaging together with long distance water-dipping lenses (Leica HXC APO 10×0.3 W, 20×0.5 W, 40×0.8 W), using filtered saline as an immersion liquid. For visualization of blood vessels, Texas Red (100 µl of 10 mg/ml; Molecular Probes, Eugene, Oreg.) was intravenously injected via the tail vein. GFP and Texas Red were excited at 890 nm and emission light was collected and separated onto two nondescanned detectors using a dicronic mirror (RSP560) and emission filters (BP 525/50 and BP 640/20). The images captured with TPLSM were denoised using wavelet filtering as previously described (27). For visualization of cell death, 100 µl of annexin V-APC (Molecular Probes) were intravenously injected via the tail vein. GFP was excited at 488 nm (35% AOTF) and emission light was collected between 495-530 nm. Reflected light was imaged by illumination at 546 nm (35% AOTF) and collection between 539-547 nm. APC was excited at 633 nm (75% AOTF), with collection of emission light between 644-680 nm. Initial studies showed weak annexin V-APC labelling of RIPGFP islet grafts ~40 min after administration with a gradual increase. The islet grafts were imaged 4-6 h after administration of annexin V-APC. The image stacks captured with CLSM were denoised using median filtering. All displayed fluorescence images have been subjected to changes in brightness and contrast for optimal visualization.

Generation of RIP-GFP mice. RIP-GFP mice were generated by injections of the RIP1.EGFP expression cassette (rat insulin-1 promoter −410/+1bp-EGFPSV40polyA) into one-cell stage embryos from B6CBAF1/Cr1 donors. The obtained F0 generation was scored for RIP1.EGFP genomic integration by PCR analysis. The RIP1.EGFP transgene was observed in seven potential transgenic founders (17.5%), which were mated with inbred C57Bl/6NCr1 mice to generate F1 animals. The founder lines were screened with regards to 1) the expression of GFP in β-cells as determined by immunostaining, and 2) animal and cell physiology. The RIP1.EGFP founder line #29 was found to have a normal glucose tolerance when compared to control animals and β-cell restricted expression of GFP, and was selected for homozygote breeding.

Immunohistochemistry. Mice were killed by exposure to a rising concentration of CO2 followed by cervical dislocation, after 3, 7, 14, and 28 days subsequent to intraocular islet transplantation (n=12). The graft-bearing eyes were removed and postfixed for 1 h in 4% paraformaldehyde. After cryoprotection by sucrose substitution (10%, 20%, and 30% in PBS), vertical sections of the eyes were cut on a cryostat (14 µm). Sections were washed in PBS (3×10 min) and incubated in PBS containing 5% bovine serum albumin and 0.1% triton (1 h). Thereafter, sections were incubated overnight in PBS with anti insulin (1:500, Accurate Chemical & Scientific Corp., NY), and anti glucagon (1:5000; Sigma, St Louis Mo.). Immunostaining was visualized using either Alexa 488 or Alexa 568 conjugated secondary antibodies (1:500; Molecular Probes). Cell nuclei were stained with DAPI (Molecular Probes). Slides were mounted with Vectamount and coverslipped. Serial cross sections of eyes containing islets were examined for the presence of insulin and glucagon with an Axiophot fluorescence microscope (Zeiss, Oberkochen, Germany) and a dual-channel laser scanning confocal microscope (Olympus Fluoview, Olympus America Inc., Melville, N.Y.). All immunostaining images were digitally acquired and recompiled (Photoshop 5.0; Adobe, San Jose, Calif.). Sections were viewed at 10× and 40× magnification. Analyses were done on digitized fluorescence microscopic images using Zeiss Axiovision software. Measured parameters (e.g. ratio insulinimmunoreactive cells/glucagon-immunoreactive cells) were calculated as the average from at least three adjacent sections from at least two separate islets per eye. The results from three eyes were averaged. Only cells that had a clearly labeled nucleus (DAPI staining) were included in the analyses. Data are presented as mean±SEM.

Quantification of islet graft vasculature. The vessel density was determined as the number of vessel segments per graft area. A vessel segment was defined as a single vessel or a branch of a vessel. The β-cell GFP fluorescence was used to define the graft area. Two optical sections were quantified from each islet graft. The optical sections were selected from image series of z-stacks. The first section was selected at the deepest level in the graft, without loss of signal. The second section was selected in the middle of the graft, between the surface and the deepest section. The images for quantification were captured using 10× or 20× lenses and a zoom factor of 2.0 or greater. Data are presented as mean±SEM. The quantification of the vasculature was made with the Leica Confocal Software (version 2.61).

In vivo recording of $[Ca^{2+}]_i$ changes. To assess function of β-cells in vivo, islets transplanted to the anterior chamber of the eye were loaded with a mixture of the $Ca^{2+}$ indicators Fluo-4 and Fura-Red. Applying these two dyes simultaneously allowed ratiometric $[Ca^{2+}]_i$ measurements with excitation spectra in the visible wavelengths (29). To achieve loading, the anterior chamber was perfused with an extracellular solution consisting of (in mM) 140 NaCl, 5 KCl, 2 $NaHCO_3$, 1 $NaH_2PO_4$, 1.2 $MgCl_2$, 2.5 $CaCl_2$, 10 HEPES, 3 glucose (pH 7.4 with KOH), containing 500 μM of each AM ester of Fluo-4 and Fura-Red. For perfusion, mice were anesthetized with 10 ml/kg of a mixture of 1 part Hypnorm (0.315 mg/ml fentanyl and 10 mg/ml fluanisone, VetaPharma, Leeds, UK), 1 part Dormicum (5 mg/ml, Roche, Basel Switzerland) and 2 parts sterile water. To prolong anesthesia, subsequent injections of the mixture (4 ml/kg) were administered every 30-40 min. Mice were placed on the microscope setup as described above, and body temperature was controlled via a rectal probe connected to the control unit of the heating pad. Micropipettes were pulled from borosilicate glass capillaries on a horizontal programmable puller (DMZ Universal Puller, Zeitz-Instrumente, Augsburg, Germany) and broken to a tip outer diameter of 60-100 μm. Adjacent micropipette tips were bevelled at an angle of 30° using a rotating wheel grinder (model BV10, Sutter Instruments Co., Novato, Calif., USA). Micropipettes were introduced into the anterior chamber by penetrating the cornea at shallow angles on opposite sides of the eye using two micromanipulator units (Eppendorf, Hamburg, Germany). Care was taken not to damage the iris or islet grafts. One micropipette was attached to a reservoir filled with extracellular solution via polyethylene tubing. The height of the reservoir was adjusted to assure a constant intracameral pressure of about 15 mmHg. The second micropipette was connected to a 1 ml syringe. Rate and volume of inflow was controlled by a syringe pump (Univector). Islet cells were loaded with $Ca^{2+}$ indicators by perfusing the anterior chamber with extracellular solution containing Fluo-4 and Fura-Red AM esters for 40 min at 3 μl/min. Subsequently, the dye containing solution was washed out by perfusion with extracellular solution for 10 min at 5-6 μl/min. Imaging was performed as described above exciting Fluo-4 and Fura-Red at 488 nm (25% AOTF) and collecting emission light for Fluo-4 between 495-535 nm and for Fura-Red between 600-700 nm. Systemic stimulation of insulin release was achieved by intravenous injection of glibenclamide (1 mg/kg) via the tail vein. After finishing imaging, mice were subcutaneously injected with 0.1 ml/kg of Temgesic (Schering-Plough, NJ) to relieve post-operative pain.

Results

Pancreatic islets are hardly accessible for in vivo monitoring because they are deeply embedded and scattered in the exocrine tissue of the pancreas, constituting 1-2% of the pancreatic volume5. As a consequence, the majority of today's functional β-cell studies are conducted in vitro on isolated islets/cells. Isolated islets (6) and especially pancreatic slices (7) allow functional studies of β-cells in a multi-cellular environment. However, these preparations are restricted to defined end-points and partially lack input from vascular and nervous connections. There is an immediate need to monitor β-cell function in vivo to understand the complex signalling networks involved in the regulation of insulin release under normal conditions, and why these do not function properly in type 2 diabetes. This is also the case in the context of clinical islet transplantation, which is emerging as a therapy for type 1 diabetes (8.) To date, monitoring β-cell signal-transduction after experimental and clinical islet transplantation has not been possible, which has severely hampered both the characterization of the graft function and the evaluation of new interventions (9). LSM has been successfully applied for imaging of multiple signaling pathways in the β-cell using isolated islets and cell preparations (6,10). However, intravital applications of LSM for studies of β-cell physiology have not been reported.

After islet transplantation, islets recruit a new vasculature (11) as well as nervous Connections (12), and are capable of maintaining glucose homeostasis via pulsatile insulin release (12,13). We decided to transplant pancreatic islets into the anterior chamber of the eye because the cornea acts as a natural body window that allows noninvasive imaging of engrafted tissue. The anterior chamber of the eye has been frequently used as a transplantation site to study a variety of tissues including pancreas because it is immune privileged (14-17). Mouse islets were transplanted into the anterior chamber of the eye via injection through the cornea (FIG. 1a). After transplantation, the islets engrafted on the iris and were readily observed and imaged through the cornea (FIG. 1b-c). The transplanted islets engrafted either as single islets or in groups as islet clusters. Immunohistochemical staining of engrafted islets showed that the proportion of the insulin-containing β-cells and glucagon-containing β-cells did not change after transplantation and that this proportion was similar to that of islets in the pancreas (FIG. 1d-h), which is in agreement with earlier Studies (14,16,17).

In mice that were rendered diabetic with streptozotocin, transplanting islets into the anterior chamber reversed hyperglycaemia. These mice further showed physiological responses to glucose challenges (FIG. 1i), demonstrating that islets engrafted in the anterior chamber of the eye are functional. To allow identification of β-cells, islets isolated from transgenic mice expressing the enhanced green fluorescent protein (GFP) under the control of the rat insulin 1 promoter (RIP-GFP) were transplanted into the anterior chamber of the eye.

Figure 2:
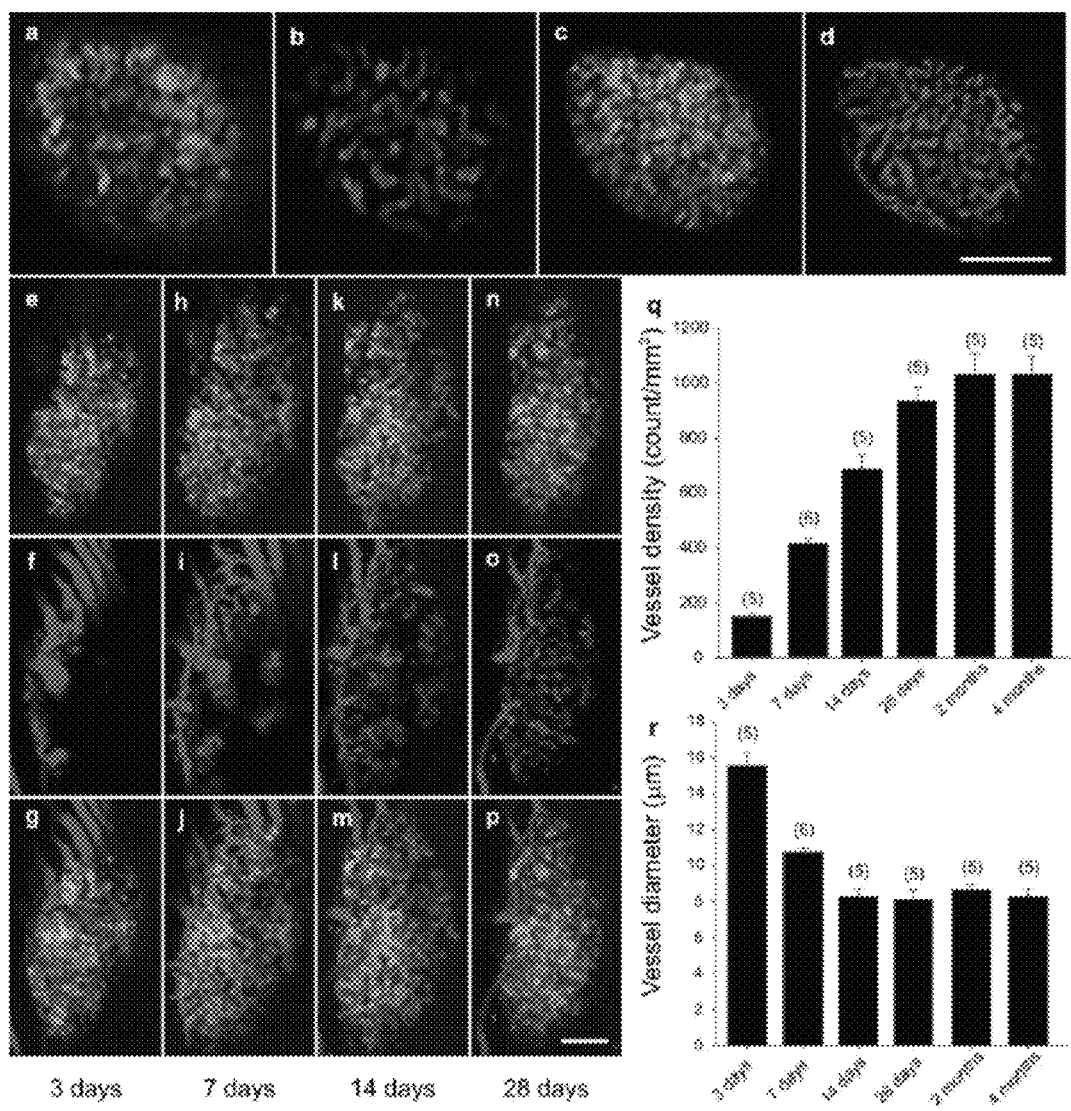
FIG. 2. Non-invasive imaging of islet engraftment and vascularization. Images of an individual RIP-GFP islet graft 4 months after transplantation (optical section captured at a depth of 51 μm). (a) β-cell GFP fluorescence (green), (b) intravenously injected Texas Red fluorescence (red), and (c-d) 2D projection of an image stack corresponding to 100 μm thickness. (e-p) Image projections (110 μm thick) of an individual RIP-GFP islet graft at day 3, 7, 14 and 28 after transplantation. GFP fluorescence of β-cells (e,h,k,n) and Texas Red fluorescence in blood vessels (f,i,l,o) are displayed separately and as an overlay (g,j,m,p). Scale bars, 100 μm. (q-r) Quantification of results shown in (e-p) The number of analyzed islet grafts is indicated in brackets at respective time-points.

By using two-photon LSM (TPLSM) we imaged simultaneously β-cells by GFP and the vasculature following intravenous injection of 100 μl Texas Red 70 kDa dextran (Texas Red, 10 mg/ml) and determined that transplanted islets recruited blood vessels from the iris. Non-invasive TPLSM enabled capturing of optical sections at different depths in the engrafted islets (FIG. 2a,b), and thereby 3D (3-dimensional) reconstruction of both the β-cell and the vascular morphology within the islet grafts (FIG. 2c-d). To monitor the dynamics of islet engraftment and vascularization, the same RIP-GFP islets were repeatedly imaged at day 3, 7, 14 and 28 after transplantation (FIG. 2e-p). At day 3, the transplanted islets were attached to the iris and structural rearrangements of iris vessels in the vicinity of the islets were observed. However, only few vessels were found to have grown into the peripheral regions of the islets (FIG. 2e-g). At day 7, the islet grafts appeared thinner but wider compared to day 3, indicating that the islets had further attached and spread out onto the iris. An increased number of blood vessels were found in the islets and capillary loops were found to start penetrating the central islet regions (FIG.

Figure 5:
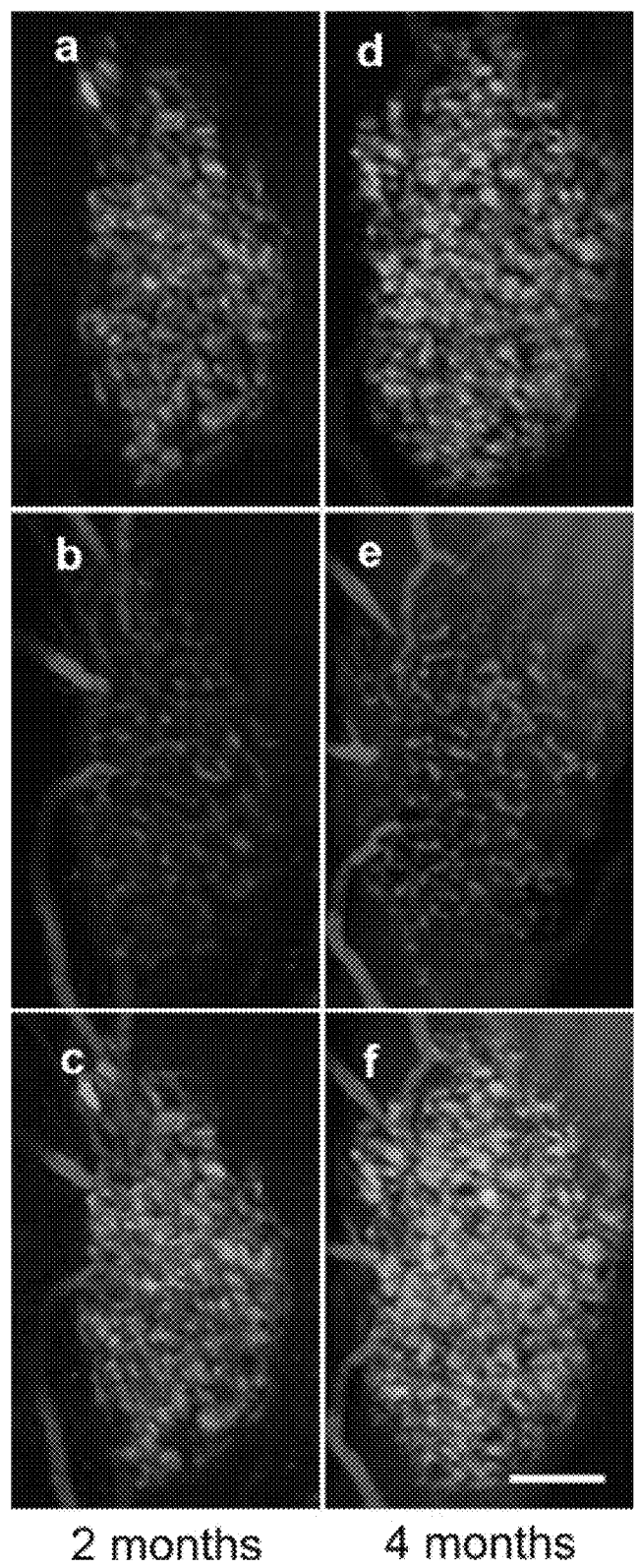
FIG. 5. Non-invasive imaging of islet engraftment and vascularization. (a-f) Image projections (110 μm thick) of the same RIP-GFP islet graft as displayed in FIG. 2 are shown at 2 and 4 months after transplantation. GFP fluorescence of β-cells (a,d) and Texas Red fluorescence in blood vessels (b,e) are displayed separately and as an overlay (c,f). Scale bar, 100 μm.

2h-j). While only minor additional changes in islet structure occurred after day 7, blood vessels continued to grow, and at day 14 they formed a microvascular network throughout the islet grafts (FIG. 2k-m). Between day 14 and day 28, the vascular network became denser, and at day 28 it was characterized by highly tortuous and uniformly sized capillaries (FIG. 2n-p). The vessel density of the transplanted islets continuously increased during revascularization (FIG. 2q). The diameter of islet graft vessels was 8.11±0.53 μm at day 28 (n=5, FIG. 2r), which is similar to the intra-islet vasculature in the pancreas (18) and at other transplantation sites (19). Imaging of islet grafts at two and four months after transplantation showed that the morphology of the β-cell mass and the graft vasculature were similar compared to day 28 (FIG. 5). In conclusion, non-invasive TPLSM enabled longitudinal in vivo imaging of β-cells and the vasculature in islets engrafted in the anterior chamber of the eye.

Figure 3:
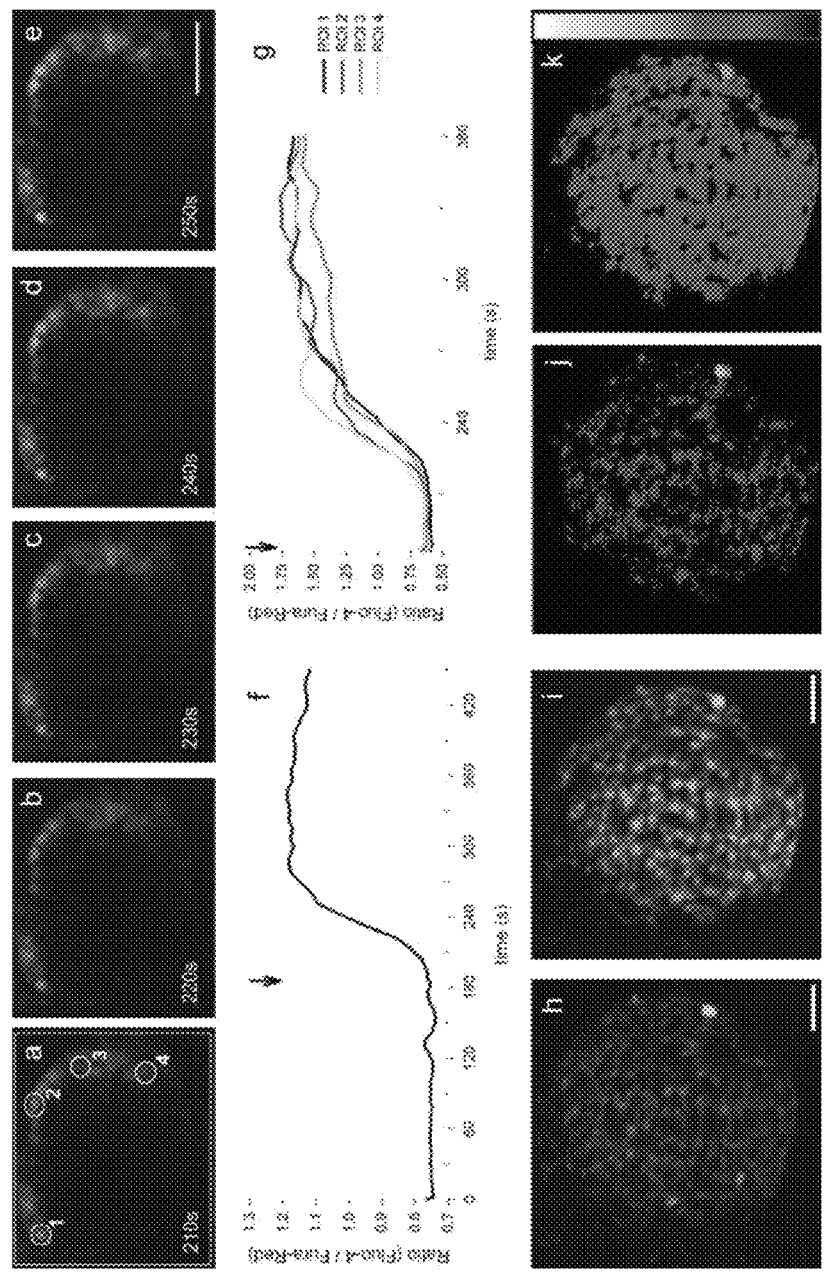
FIG. 3. In vivo imaging of β-cell function. (a-e) Fluorescence images of Fluo-4 and Fura-Red at indicated time points after systemic application of glibenclamide (1 mg/kg) at 3 min. (f) Whole frame Fluo-4/Fura-Red ratio change in response to given glibenclamide stimulus, start of stimulation indicated by arrow. (g) Ratio change in individual cells throughout the islet as indicated in panel (a). (h-i) Maximum projections of Fluo-4 (green) and Fura-Red (red) fluorescence of a whole islet before (h) and after stimulation with glibenclamide (i). (j-k) Ratiometric display of Fluo-4/Fura-Red of the islet in panel (h) and (i). Scale bar, 50 μm.
Figure 4:
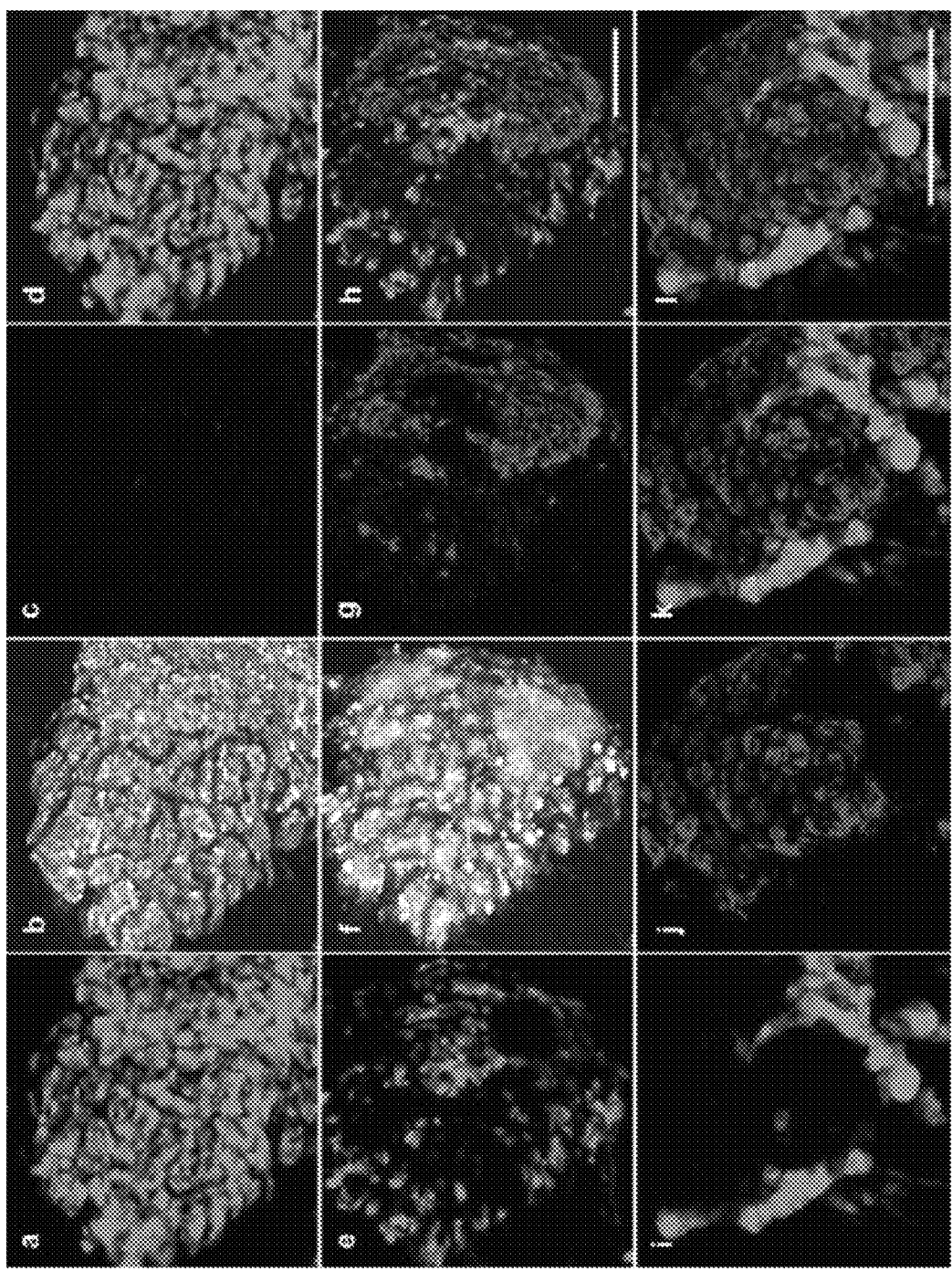
FIG. 4. Non-invasive in vivo imaging of β-cell death. (a-h) Image projections of an individual RIP-GFP islet graft in the anterior chamber of the eye. Under normal conditions, (a) β-cell GFP fluorescence, (b) reflection from the endocrine cells and (c) undetectable annexin V-APC labelling of the graft. (d) Overlay image of (a-c) with the reflection image in blue. Twenty-four hours after induction of β-cell death, (e) β-cell GFP fluorescence, (f) reflection and (g) strong annexin V-APC fluorescence of the islet graft. (h) Overlay image of (e-g) with the reflection image in blue. (i-j) High magnification images of an islet graft area strongly labelled with annexin V-APC after induction of β-cell death. (i) β-cell GFP fluorescence, (j) annexin V-APC fluorescence and (k) overlay of (i-j). (l) Overlay of (k) with the reflection image (blue). Scale bars, 100 μm.

The assessment of signal-transduction in vivo at the cellular level would allow investigation of islet cells under both physiological and pathophysiological conditions, including regulatory and modulatory influences from paracrine, hormonal, and neuronal signals. To monitor cell function in vivo, we studied changes in cytoplasmatic free calcium concentration ([Ca2+]i) in islets at the single cell level in the anterior chamber of the eye. Changes in [Ca2+]i are key intracellular signals in islet cells and serve as a reporter of β-cell function2. We loaded islets with the Ca2+ indicators Fluo-4 and Fura-Red via perfusion of the anterior chamber of the eye with micropipettes. Applying these two dyes simultaneously allowed ratiometric measurements of [Ca2+]i changes with LSM and correction for movements of the islets during imaging. Fluo-4 and Fura-Red labelled the outer layer of the islets homogenously (FIG. 3h-i). To stimulate cells, we applied the sulfonylurea compound glibenclamide intravenously. This decreased blood glucose levels, indicating that the administration was effective (data not shown). Increases in [Ca2+]i in islet cells, as demonstrated by prominent rises in the Fluo-4/Fura-Red fluorescence ratio, started within 30 to 40 seconds after glibenclamide injection into the tail vein of the mouse and remained high throughout the recording (FIG. 3f). [Ca2+]i increased simultaneously in different regions of the islets, reflecting a synchronized response of β-cells within an islet after stimulation20 (FIG. 3g). These results demonstrate that it is feasible to image islet cell function in vivo employing engrafted islets in the anterior chamber of the eye.

β-cell death is a characteristics of type 1 diabetes (21) and is implicated in the pathology of type 2 diabetes (22). To date, no methods exist for continuous monitoring of β-cell death in vivo. Annexin V has been used as a reporter of cell death both under experimental and clinical conditions (23) and has been validated as a marker for β-cell apoptosis after systemic administration (24). To investigate the feasibility of noninvasive imaging of β-cell death, we transplanted RIP-GFP islets into the anterior chamber of the eye and, after complete engraftment and revascularization, we monitored cell death following intravenously administered annexin V conjugated to allophycocyanin (APC). Using confocal LSM, GFP- and annexin V-APC fluorescence were captured simultaneously with reflected light, whereby the latter provides detailed structural information of endocrine cells (25). Transplanted RIP-GFP islets imaged in mice with regular blood glucose levels displayed normal morphology (FIG. 4a-b) and absence of annexin V-APC labelling (FIG. 4c-d). Annexin VAPC was only found to label a few cells in 1 out of 10 RIP-GFP islet grafts (data not shown), indicating a low incidence of cell death in islets engrafted in the anterior chamber of the eye. We induced β-cell death in mice transplanted with RIP-GFP islets by intravenous administration of alloxan (75 mg/kg), a well-characterized diabetogenic compound that is taken up by β-cells via the glucose transporter 2 (26). This treatment rendered mice hyperglycemic with a blood glucose concentration of 25.0±1.3 mmol/l (n=6) after 24 h. At this time-point, substantial loss of GFP fluorescence and structural changes in the reflection of the islet grafts were observed (FIG. 4e-f), indicating loss of β-cells. Administration of annexin V-APC (n=4) 24 h after the induction of cell death resulted in strong labelling of islet grafts (FIG. 4gh). High magnification imaging revealed that most annexin V-APC labelling was found in graft regions devoid of GFP fluorescence. Some annexin V-APC fluorescence was found on the surface of GFP-fluorescent β-cells, indicating labeling of cells undergoing apoptosis (FIG. 4i-l). We conclude that β-cell death can be imaged non-invasively and longitudinally under in vivo conditions in islets engrafted in the anterior chamber of the eye.

Summary

We have now introduced a novel platform for non-invasive studies of islet cell both physiology and pathophysiology in vivo. Employing the anterior chamber of the eye as an in vivo model for islet cell research enables the continuous monitoring of morphology, vascularisation, innervation, cell death, and cell signalling. The use of this platform to study islet cell signal-transduction in vivo will help elucidating the effects of modulatory inputs from the hormonal and neuronal system, as well as from autocrine/paracrine signals of endocrine or vascular cells. Furthermore, it will serve as a novel approach for non-invasive in vivo studies of β-cell function and survival under healthy and diabetic conditions. Noteworthy is, that this platform is not limited to studies of pancreatic β-cell signal-transduction but can readily be extended to investigate numerous other cell types and organ tissues in vivo. Hence, the anterior chamber of the eye can be used as a versatile natural body window to clarify, for the first time, the integration of complex signalling networks at the cellular level under in vivo conditions.

REFERENCES FOR EXAMPLE 1

1. Wajchenberg, B. L. Beta-Cell Failure in Diabetes and Preservation by Clinical Treatment. *Endocr Rev* (2007).
2. Berggren, P. O. & Leibiger, I. B. Novel aspects on signal-transduction in the pancreatic beta-cell. *Nutr Metab Cardiovasc Dis* 16 Suppl 1, S7-10 (2006).
3. Vetterlein, F., Petho, A. & Schmidt, G. Morphometric investigation of the microvascular system of pancreatic exocrine and endocrine tissue in the rat. *Microvasc Res* 34, 231-8 (1987).
4. Woods, S. C. & Porte, D., Jr. Neural control of the endocrine pancreas. *Physiol Rev* 54, 596-619 (1974).
5. Rahier, J., Goebbels, R. M. & Henquin, J. C. Cellular composition of the human diabetic pancreas. *Diabetologia* 24, 366-71 (1983).
6. Köhler, M. et al. Imaging of Pancreatic Beta-Cell Signal-Transduction. *Curr. Med. Chem.-Immun., Endoc. & Metab. Agents* 4, 281-299 (2004).
7. Speier, S. & Rupnik, M. A novel approach to in situ characterization of pancreatic beta-cells. *Pflugers Arch* 446, 553-8 (2003).

8. Shapiro, A. M. et al. Islet transplantation in seven patients with type 1 diabetes mellitus using a glucocorticoid-free immunosuppressive regimen. *N Engl J Med* 343, 230-8 (2000).
9. Paty, B. W., Bonner-Weir, S., Laughlin, M. R., McEwan, A. J. & Shapiro, A. M. Toward development of imaging modalities for islets after transplantation: insights from the National Institutes of Health Workshop on Beta Cell Imaging. *Transplantation* 77, 1133-7 (2004).
10. Philipson, L. H. & Roe, M. W. Imaging. *Curr. Med. Chem.-Immun., Endoc. & Metab. Agents* 4, 333-337 (2004).
11. Menger, M. D., Yamauchi, J. & Vollmar, B. Revascularization and microcirculation of freely grafted islets of Langerhans. *World J Surg* 25, 509-15 (2001).
12. Porksen, N. et al. Coordinate pulsatile insulin secretion by chronic intraportally transplanted islets in the isolated perfused rat liver. *J Clin Invest* 94, 219-27 (1994).
13. Meier, J. J. et al. Intrahepatic transplanted islets in humans secrete insulin in a coordinate pulsatile manner directly into the liver. *Diabetes* 55, 2324-32 (2006).
14. Hultquist, G. T. The ultrastructure of pancreatic tissue from duct-ligated rats implanted into anterior chamber of rat eyes. *Ups J Med Sci* 77, 8-18 (1972).
15. Niederkorn, J. Y. Immune privilege in the anterior chamber of the eye. *Crit Rev Immunol* 22, 13-46 (2002).
16. Adeghate, E. & Donath, T. Morphological findings in long-term pancreatic tissue transplants in the anterior eye chamber of rats. *Pancreas* 5, 298-305 (1990).
17. Adeghate, E., Ponery, A. S., Ahmed, I. & Donath, T. Comparative morphology and biochemistry of pancreatic tissue fragments transplanted into the anterior eye chamber and subcutaneous regions of the rat. *Eur J Morphol* 39, 257-68 (2001).
18. Vetterlein, F., Petho, A. & Schmidt, G. Distribution of capillary blood flow in rat kidney during postischemic renal failure. *Am J Physiol* 251, H510-9 (1986).
19. Menger, M. D., Vajkoczy, P., Leiderer, R., Jager, S. & Messmer, K. Influence of experimental hyperglycemia on microvascular blood perfusion of pancreatic islet isografts. *J Clin Invest* 90, 1361-9 (1992).
20. Valdeolmillos, M., Santos, R. M., Contreras, D., Soria, B. & Rosario, L. M. Glucose-induced oscillations of intracellular Ca2+ concentration resembling bursting electrical activity in single mouse islets of Langerhans. *FEBS Lett* 259, 19-23 (1989).
21. Mathis, D., Vence, L. & Benoist, C. beta-Cell death during progression to diabetes. *Nature* 414, 792-8 (2001).
22. Butler, A. E. et al. Beta-cell deficit and increased beta-cell apoptosis in humans with type 2 diabetes. *Diabetes* 52, 102-10 (2003).
23. Boersma, H. H. et al. Past, present, and future of annexin A5: from protein discovery to clinical applications. *J Nucl Med* 46, 2035-50 (2005).
24. Medarova, Z., Bonner-Weir, S., Lipes, M. & Moore, A. Imaging beta-cell death with a near-infrared probe. *Diabetes* 54, 1780-8 (2005).
25. Nyqvist, D., Köhler, M., Wahlstedt, H. & Berggren, P. O. Donor islet endothelial cells participate in formation of functional vessels within pancreatic islet grafts. *Diabetes* 54, 2287-93 (2005).
26. Szkudelski, T. The mechanism of alloxan and streptozotocin action in B cells of the rat pancreas. *Physiol Res* 50, 537-46 (2001).
27. Köhler, M. et al. On-line monitoring of apoptosis in insulin-secreting cells. *Diabetes* 52, 2943-50 (2003).
28. Lipp, P. & Niggli, E. Ratiometric confocal Ca(2+)-measurements with visible wavelength indicators in isolated cardiac myocytes. *Cell Calcium* 14, 359-72 (1993).

EXAMPLE 2

In this example, we provide a step-by-step protocol for non-invasive longitudinal in vivo studies of cell biology at single-cell resolution, taking advantage of the cornea as a natural body window. For this purpose, the tissue of interest is transplanted into the anterior chamber of the eye and cell biological parameters are assessed by LSM through the cornea. The anterior chamber of the eye has been frequently used as a transplantation site to study a variety of tissues[3-7]. While originally the anterior chamber of the eye was selected as a transplantation site because of its properties as an immune privileged site[8], most studies utilized the anterior chamber in a syngeneic transplantation setting because it is easily accessible and the cornea allows macroscopic observation of the engrafted tissue. Additionally, the iris, which forms the base of the anterior chamber, has one of the highest concentrations of blood vessels and autonomic nerves in the body, and thereby enables fast innervation[9] and vascularization[10] of the graft. Up to date studies utilizing the anterior chamber as a transplantation site mainly employed macroscopic observations[5] to investigate graft physiology. This restricts longitudinal studies to parameters observable at low resolution. In vivo electrophysiology[7] as well as histology[3] and various other in vitro techniques after graft removal enable assessment of morphology and cellular function, however setting an endpoint to the study and hereby preventing longitudinal monitoring.

Materials

Animals

NMRI mice (Charles River Laboratories, USA) or (Scanbur, Sweden)

Tie2-GFP mice [STOCK Tg(TIE2GFP)287Sato/J] (Jackson Laboratory, USA)

Transgenic mice with fluorescent reporters expressed in pancreatic beta-cells under the insulin promoter (RIP-GFP)[11].

Reagents

Sterile phosphate buffered saline (PBS)

Isoflurane (Isoflurane, Abott/Baxter, USA)

40% $O_2$ in 60% $N_2$ (AGA, Sweden)

Butrenorphine (Temgesic, Schering-Plough, USA)

Viscotears® (Novartis, Switzerland)

Alloxan (Sigma, USA)

Texas Red 70 kDa dextran (Invitrogen, USA)

Annexin V APC (Invitrogen, USA)

Hypnorm® (VetaPharm, UK)

Dormicum® (Roche, Switzerland)

Sterile water for injection (Braun, Germany)

Fluo-4 AM special packaging (Invitrogen, USA)

Fura-Red AM special packaging (Invitrogen, USA)

Pluronic® F-127 (Invitrogen, USA)

Glibenclamide (Sigma, USA)

Extracellular solution

Reagent Setup

Extracellular solution (in mM): 140 NaCl, 5 KCl, 2 $NaHCO_3$, 1 $NaH_2PO_4$, 1.2 $MgCl_2$, 2.5 $CaCl_2$, 10 HEPES, 3 glucose (pH 7.4 with NaOH).

Equipment

27 G×¾" needle (BD, USA)

Blunt 27 G cannula, custom made of a 27 G needle 0.5 ml threaded plunger Hamilton gastight syringe #1750 (Hamilton, USA)

polythene tubing 0.4 mm inner diameter (i.d.), 0.8 mm outer diameter (o.d.) (Smiths Medical, UK)
polythene tubing 0.2 mm i.d., 0.8 mm o.d.
polythene tubing 0.9 mm i.d., 1.2 mm o.d.
tygon tubing 0.76 mm i.d., 0.86 mm wall thickness (Ismatec, Switzerland)
1, 5 and 10 ml plastic syringes (BD, USA)
50 ml reagent tube (Eppendorf, Germany)
400 Anesthesia Unit (Univentor, Malta)
Exmire Microsyringe MS-GLLX00 10 ml (Hamilton, USA)
Stereomicroscope MZ FLIII (Leica, Germany)
Head holding adapter (SG-4N, Narishige, Japan)
UST-2 Solid Universal Joint (Narishige, Japan)
Dumont #5 Forceps (Fine Science Tools, USA)
Custom-made heating pad
DMLFSA upright microscope, equipped with a TCS-SP2-AOBS confocal scanner (Leica, Germany)
Ti:Sapphire laser Tsunami (Spectra-Physics, USA)
2.5× and 5× objectives (Leica, Germany)
long distance water-dipping lenses (Leica HXC APO 10×0.3 W, 20×0.5 W, 40×0.8 W)
Micromanipulator 5171 (2) (Eppendorf, Germany)
Universal capillary holder (2) (Eppendorf, Germany)
Capillary grip head 1 (2) (Eppendorf, Germany)
Thin-wall borosilicate glass capillaries without filament TW120-4 (WPI, USA)
DMZ universal puller (Zeitz Instrumente, Germany)
802 syringe pump (Univentor, Malta)
Leica Confocal Software (version 2.61) (Leica, Germany)
Volocity (Improvision, UK)
Matlab (The MathWorks, USA)
Wavelet filtering algorithm[14] (Stockholm, Sweden)

Equipment Setup

Confocal and Two-Photon Setup

For LSM we use a Leica TCS-SP2-AOBS confocal laser scanner equipped with Argon and HeNe lasers connected to a Leica DMLFSA microscope. Two-photon excitation is achieved using a Ti:Sapphire laser (Tsunami; Spectra-Physics, USA) for ~100 fs excitation at ~82 MHz. The microscope stage is customized for the use of head holding adaptor and mouse.

Head Holding Adapter

To fix the head of the mouse for surgery and imaging, we employ a head holding adapter SG-4N-S manufactured by Narishige, Japan. Depending on the type of anesthesia used the head holder is equipped with a gas mask (GM-4-S) or a nosepiece. The head holder is attached to a metal plate which fits onto the customized stage of the microscope. The metal plate is covered by a heating pad. Body temperature is controlled via a rectal probe which regulates the temperature of the heating pad.

Eye Stabilizer

For retraction of the eye lids and additional stabilization of the eye we use a custom-made supporting device. Attach a #5 Dumont forceps to a small metal bar and clamp the metal bar into a UST-2 Solid Universal Joint. Fix the Universal Joint to the same metal plate as the head holder on level with the eye, so you can reach the eyes with the tips of the forceps. Cover the tips of the forceps with a piece of polyethylene tube, creating a loop between the tips. At the front part of the forceps attach a screw to enable adjustment of the distance between the forceps tips.

Anterior Chamber Perfusion

Outflow: Connect a ~35 cm piece of polythene tubing 0.9 mm i.d. and 1.2 mm o.d. with one end to a capillary holder and connect the other end of the tubing to a 10 ml syringe without a plunger (open reservoir).

Inflow: Connect a ~35 cm piece of tygon tubing 0.76 mm i.d. and 0.86 mm wall thickness with one end to a capillary holder and connect the other end of the tubing to a 1 ml syringe.

Image Processing

To denoise images captured with confocal LSM and TPLSM use wavelet filtering[15]. For analysis and image display use processing software e.g. Volocity and Leica confocal software.

Non-Limiting, Exemplary Procedure

Transplantation of Pancreatic Islets to the Anterior Chamber of the Eye

1 Isolate mouse pancreatic islets as previously described[16,17].

Optionally culture islets, depending on study parameters.

2 Connect about 10 cm of 0.4 mm i.d. polythene tubing with a 27 G needle to the 0.5 ml Hamilton syringe and insert the blunt 27 G cannula at the other end of the tubing.

3 Transfer 30-40 islets from the culture medium to a dish with sterile PBS and center the islets as compact as possible in the middle of the dish.

4 Aspirate the islets into the blunt 27 G cannula and the connected polythene tubing. The islets are preferably aspirated in a minimal volume (for example, 20 µl or less) to facilitate injection into the anterior chamber.

Aspirating the islets into too big a volume may lead to difficulties during the injection process by exposing the eye to unnecessary high intraocular pressure and may result in reflux of islets out of the anterior chamber after removing the cannula.

5 Carry out the transplantation of islets to the anterior chamber of the eye according to option (A) or (B).

(A) Transplantation of Islets Using a Head Holder.

i Put a piece of cotton wool in a 50 ml reagent tube and drop about 1 ml Isoflurane onto the wool. Stun the mouse by holding it for a few seconds into the reagent tube.

ii Place the mouse in the head holder under a stereomicroscope and fix the head with the eye selected for transplantation facing upwards.

iii Anesthetize the mouse using Isoflurane, 2-2.5% in 40% $O_2$ and 60% $N_2$. Isoflurane levels are carefully controlled to ensure a proper state of anesthesia. Vacuum is applied in the area of anesthesia to protect the operator.

iv Inject butrenorphine (0.05 mg/kg) subcutaneously to relieve post-operative pain.

v Carefully pull back the eyelids and gently place the polyethylene tubing loop of the eye stabilizer below the corneoscleral junction.

Care is taken when placing the stabilizing forceps to avoid disrupting blood circulation in the eye.

vi Connect a 27 G needle to a 1 ml syringe to ease handling. Use the 27 G needle to puncture the cornea close to the sclera while taking care not to damage the iris and to avoid bleeding.

vii Gently insert the blunt cannula into the anterior chamber of the eye through the hole made with the needle. Slowly inject the islets into the anterior chamber. After injection, carefully withdraw the cannula.

viii Leave the mouse in the head holder before awakening for additional 10-15 min. Remove the mouse from the head holder, turn off the Isoflurane and observe the mouse during awakening.

ix Put a drop of Viscotears on the eye to prevent desiccation.
   A break is made until the in vivo imaging. The duration depends on study parameters.
(B) Transplantation of Islets without Using the Head Holder.
   i Prepare a small gas mask from a 5 ml plastic syringe by removing the piston and cutting the syringe ~1 cm above the bottom. Connect the tubing of the anesthetic pump to the needle fitting.
   ii Stun the mouse by holding it for a few seconds into the 50 ml reagent tube with cotton and about 1 ml Isoflurane.
   iii Place the mouse under a stereomicroscope on a heating pad with the eye selected for transplantation facing upwards. Put the nose of the mouse in the prepared gas mask.
   iv Anesthetize the mouse using Isoflurane, 2-2.5% in 40% $O_2$ and 60% $N_2$.
      Isoflurane levels are carefully controlled to ensure a proper state of anesthesia. Vacuum is applied in the area of anesthesia to protect the operator.
   v Inject butrenorphine (0.05 mg/kg) subcutaneously to relieve post-operative pain.
   vi Retract the skin around the eye to visualize the corneoscleral junction of the eye and gently fix the position of the head, without interrupting the breathing or blood circulation of the mouse.
   vii Continue as described above under (A) from point vi to ix.

Imaging of Islets Engrafted in the Anterior Chamber of the Eye
6 Transplant islets according to steps 1-5. Choose donor and recipient mice depending on the aim of the study.
7 Stun the recipient mouse by short exposure to Isoflurane.
8 Place the mouse in the head holder and fix the head with the eye containing the transplanted islets facing upwards.
9 Anesthetize the mouse using Isoflurane, 2-2.5% in 40% $O_2$ and 60% $N_2$.
   Isoflurane levels are carefully controlled to ensure a proper state of anesthesia. Vacuum is applied in the area of anesthesia to protect the operator.
10 Carefully pull back the eyelids and gently place the polyethylene tubing loop of the eye stabilizer below the corneoscleral junction.
   Care is taken when placing the stabilizing forceps to not disrupt blood circulation in the eye.
11 Place the head holder together with the mouse under an upright microscope equipped for confocal and two-photon LSM.
12 To get an overview use low magnification objectives (2.5 and 5×). For high resolution LSM utilize water immersion dipping objectives (10, 20, and 40×) with a long-working distance using filtered saline or Viscotears as immersion liquid between the lens and the cornea.
   Apply the minimum required laser-power and scan-time necessary for visualization to avoid photodamage and bleaching; for example, below 75 mW, and from 800 Hz and above.
13 Image the biological parameter of interest:
   (A) Imaging of Graft Morphology
   i To visualize cell specific morphology, islets of transgenic mice expressing a fluorescent protein in beta-cells (e.g. RIP-GFP) can be used for transplantation. Excite GFP fluorescence with a 488 nm laser and detect emission between 495 and 530 nm. Islet morphology can also be imaged by detection of a reflection image.
   Choose a laser (e.g. 633 nm) and set the AOBS control to optimize reflection detection. Collect emission between ±4 nm of the laser wavelength.
(B) Imaging of Vascularization in the Iris and the Engrafted Islets
   Visualize vascularization either by imaging endothelial cells or the blood vessel lumen.
   i To image endothelial cells utilize Tie2-GFP mice for transplantation.
   ii Excite GFP fluorescence with a 488 nm laser and detect emission between 495 and 530 nm.
   iii For imaging of the blood vessel lumen inject 0.1 ml of 10 mg/ml of a fluorescently labeled dextran (70 kDa) intravenously into the tail vein.
   iv Following injection of a fluorescently labeled dextran, image the engrafted islets using appropriate settings for the chosen dextran.
      For simultaneous imaging of beta-cells and vessels transplant islets of RIP-GFP mice and inject Texas-Red conjugated dextran (70 kDa). Excite Texas Red and GFP with a two-photon laser at 890 nm and collect emission light onto non-descanned detectors using a dichroic mirror (RSP 560) and emission filters (BP 525/50 and BP 640/20).
(C) Imaging of Beta-Cell Death
   i Induce beta-cell death in the engrafted islets by intravenous injection of alloxan (75 mg/kg body weight). Wait for 24 h for alloxan to induce beta-cell death.
   ii Measure blood glucose levels 24 h after the administration of alloxan to confirm that the mouse has been rendered hyperglycemic.
   iii Inject 0.1 ml of annexin V-APC intravenously via the tail vein.
      Wait for 4-6 h for annexin V APC to label apoptotic and dead cells.
   iv Image beta-cell death in the engrafted islets between 4-6 h following the administration of annexin V-APC, using appropriate settings for APC fluorescence. Excite APC at 633 nm with collection of emission light between 645-680 nm.
(D) Imaging of Cytoplasmic Free $Ca^{2+}$ Concentration after Loading the Graft with $Ca^{2+}$ Indicators Via Perfusion of the Anterior Chamber of the Eye.
   Anterior chamber perfusion is modified from ref.[18].
   i Pull pipettes for the anterior chamber of the eye perfusion from glass capillaries using a regular pulling program for patch pipettes. Break the pipette to a tip diameter of 30-40 μm. Bevel the tips at an angle of 35 degrees to a final diameter of 70-90 μm. Pipettes for the outflow should be slightly bigger (~90 μm) than pipettes for the inflow (~70 μm).
   ii Fill the syringes, tubing and capillary holders with filtered extracellular solution and place the pipettes in the capillary grip head of the capillary holder.
   iii Anesthetize the mouse by an intraperitoneal injection of 100 μl/10 g bodyweight of a Hypnorm/sterile water/ Dormicum mix (1:2:1). Anesthesia will set in within 1-2 min. Prolong anesthesia by injections of 50 μl/10 g bodyweights of a Hypnorm/sterile water mix (1:3) after 30 and 60 min. If necessary further prolong anesthesia after 90 min by an injection of 50 μl/10 g bodyweight of the initial Hypnorm/sterile water/Dormicum mix (1:2:1).
      Care is taken in choosing an anesthetic for functional studies on islet cells, as several compounds have been reported to exert an effect on blood glucose levels and insulin secretion[19,20]. Isoflurane has been shown to inhibit glucose stimulated insulin release by a direct mechanism on islet cells and therefore is not suitable for functional studies[21]. A mix of Hypnorm/Dormicum does not seem to interfere with the measurements of changes in cytoplasmic free $Ca^{2+}$ concentration.

iv Put the mouse in the head holder and fix the head with the eye containing the transplanted islets facing upwards.

v Carefully pull back the eyelids and gently place the polyethylene tubing loop of the eye stabilizer below the corneoscleral junction and place holder and mouse under the upright microscope.

Care is taken when placing the stabilizing forceps not to disrupt blood circulation in the eye.

vi Hang the open reservoir of the outflow at a height of ~21 cm above the eye to ensure a constant intraocular pressure of ~15 mm Hg. Place the capillary holder of the outflow in the micromanipulator.

vii Employ a 2.5× objective while inserting the outflow pipette into the anterior chamber with the micromanipulator to observe the entire eye.

Penetrate the anterior chamber by moving the pipette fast through the cornea at a shallow angle. Be careful not to unnecessarily scratch the cornea or to damage the iris.

viii Aspirate ~130 µl of the Fluo-4/Fura-Red mix (1:1, 500 µM each) into the inflow capillary and fix the capillary holder onto the micromanipulator.

Make sure that there is enough dye-free extracellular solution in the syringe for wash out. Place the 1 ml syringe of the inflow into the syringe pump.

ix Insert the inflow pipette into the anterior chamber opposite to the outflow pipette. Penetrate the cornea in the same way as in step vii.

x Initially, exchange the aqueous humor with the perfusate fast (~10 µl in 30 s). Observe functionality of the perfusion.

xi Continuously perfuse the anterior chamber of the eye at a rate of ~3 µl/min for ~40 min.

xii After loading, wash out the dye in the anterior chamber by perfusing the anterior chamber at a fast rate (~10 µl/min).

During perfusion steps, control the perfusion and the eye. Pay attention that the eye is not swelling due to a blocked outflow.

xiii After wash out of the dye switch off the perfusion. Do not remove the pipettes.

xiv For imaging of changes in cytoplasmic free $Ca^{2+}$ concentration switch to a higher magnification water immersion dipping objective (10, 20 or 40×) and apply Viscotears as immersion liquid.

xv Simultaneously image Fluo-4 and Fura-Red to enable ratiometric measurements of changes in cytoplasmic free $Ca^{2+}$ concentration. Excite Fluo-4 and Fura-Red at 488 nm and collect emission light for Fluo-4 between 495-535 nm and for Fura-Red between 600-700 nm.

Apply the minimum required laser-power and scan-time necessary for visualization to avoid photodamage and bleaching; for example, below 75 mW, and from 800 Hz and above xvi Start acquiring a time series of the Fluo-4 and Fura-Red fluorescence in the cells of interest.

xvii Acquire a baseline of unstimulated fluorescence levels and stimulate systemic insulin release by injecting glibenclamide (1 mg/kg) intravenously via the tail vein. Changes in cytoplasmic free $Ca^{2+}$ concentration in beta-cells within the islet graft should be observed within seconds after injection.

xviii After imaging remove the pipettes carefully from the eye.

xix To relieve post-operative pain inject the mouse subcutaneously with butrenorphine (0.05 mg/kg).

xx Place the mouse in a warm environment (~30° C.) until it wakes up. After Hypnorm/Dormicum anesthesia this can take several hours.

Timing

Isolation of islets (step 1): ~4 h

Transplantation of islets to the anterior chamber (steps 2-5): ~25 min/mouse

Imaging of graft morphology (step 13 A): ~1 h/mouse

Imaging of graft vascularization (steps 13 B, i-ii or iii-iv): ~1 h/mouse

Imaging of beta-cell death (steps 13 C i-ii): ~24 h; (step 13 C iii-iv): ~5 h

Imaging of cytoplasmic free $Ca^{2+}$ concentration after loading the graft with $Ca^{2+}$ indicators via perfusion of the anterior chamber of the eye (step 13 D i): ~1.5 h/4-6 pipettes; (steps 13 D ii-xx): ~2 h/mouse Anticipated Results The here introduced platform enables longitudinal assessment of several biological parameters in vivo without the need of invasive surgical procedures to access the tissue of interest. Following transplantation of pancreatic islets of Langerhans to the anterior chamber of the eye, the current protocol easily enables detection of islet graft morphology by reflection or fluorescence imaging. Morphological characterization of a pancreatic islet graft by imaging reflection and GFP was carried out in which. islets of mice expressing GFP under the insulin promoter (green beta-cells) were transplanted to mice expressing GFP under the Tie2 promoter (green endothelial cells). GFP was excited with 488 nm at 35% laser power and emission measured between 495-530 nm. Reflection was imaged by exciting with 633 nm at 35% laser power and measuring emission between 632-639 nm.

Furthermore, vascularization and cell death can be followed longitudinally by systemic injections of fluorescent dyes. Blood vessels were visualized by an intravenous injection of a 70 kDa Texas Red labeled dextran. GFP and Texas Red were excited with a two-photon laser at 890 nm at minimal necessary laser power required and emission collected onto non-descanned detectors using a dichroic mirror (RSP 560) and emission filters (BP 525/50 and BP 640/20). For imaging of cell death, beta-cell death was induced by intravenous injection of alloxan. Apoptotic and dead cells were visualized by intravenous injection of annexin V-APC. Reflection was imaged by exciting with 543 nm and emission measured between 539-547 nm at 35% laser power. GFP was excited at 488 nm and emission measured between 495-530 nm at 35% laser power. APC was excited at 633 nm with collection of emission light between 645-680 nm at 75% laser power.

Additionally, islet-cells can be loaded repetitively with $Ca^{2+}$ indicators, by perfusion of the anterior chamber, to measure systemically induced changes in cytoplasmic free $Ca^{2+}$ concentration. For loading with calcium indicators, the anterior chamber was perfused with Fluo-4 and Fura-Red. Fluo-4 and Fura-Red were excited with 488 nm at 25% laser power and emission measured for Fluo-4 between 495-535 nm and for Fura-Red between 600-700 nm. Reflection was imaged by exciting with 543 nm and emission measured between 539-547 nm at 15% laser power.

Extending the current protocol by the use of various transgenic mice and indicators will enable the observation of numerous additional biological parameters. Thereby, this platform will help to investigate cell biology of complex systems under physiological as well as pathophysiological conditions.

EXAMPLE 2 REFERENCES

1. Koo, V., Hamilton, P. W. & Williamson, K. Non-invasive in vivo imaging in small animal research. *Cell Oncol* 28, 127-139 (2006).
2. *Handbook of biological confocal microscopy*, Edn. 3 (Fawley, J. B.) (Springer, New York, N.Y., 2005).
3. Adeghate, E., Ponery, A. S., Ahmed, I. & Donath, T. Comparative morphology and biochemistry of pancreatic tissue fragments transplanted into the anterior eye chamber and subcutaneous regions of the rat. *European journal of morphology* 39, 257-268 (2001).
4. Katoh, N., et al. Target-specific innervation by autonomic and sensory nerve fibers in hairy fetal skin transplanted into the anterior eye chamber of adult rat. *Cell and tissue research* 266, 259-263 (1991).
5. Olson, L. & Seiger, A. Beating intraocular hearts: light-controlled rate by autonomic innervation from host iris. *Journal of neurobiology* 7, 193-203 (1976).
6. Wu, W., Scott, D. E. & Reiter, R. J. Transplantation of the mammalian pineal gland: studies of survival, revascularization, reinnervation, and recovery of function. *Experimental neurology* 122, 88-99 (1993).
7. Hoffer, B., Seiger, A., Ljungberg, T. & Olson, L. Electrophysiological and cytological studies of brain homografts in the anterior chamber of the eye: maturation of cerebellar cortex in oculo. *Brain research* 79, 165-184 (1974).
8. Niederkorn, J. Y. Immune privilege in the anterior chamber of the eye. *Critical reviews in immunology* 22, 13-46 (2002).
9. Adeghate, E. Pancreatic tissue grafts are reinnervated by neuro-peptidergic and cholinergic nerves within five days of transplantation. *Transplant immunology* 10, 73-80 (2002).
10. Adeghate, E. Host-graft circulation and vascular morphology in pancreatic tissue transplants in rats. *The Anatomical record* 251, 448-459 (1998).
12. Zhuravleva, Z. N., Bragin, A. G. & Vinogradova, O. S. Organization of the nervous tissue (hippocampus and septum) developing in the anterior eye chamber. I. General characteristics and non-neural elements. *Journal fur Hirnforschung* 25, 313-330 (1984).
13. Adeghate, E. & Donath, T. Distribution of neuropeptide Y and vasoactive intestinal polypeptide immunoreactive nerves in normal and transplanted pancreatic tissue. *Peptides* 11, 1087-1092 (1990).
14. Boutet de Monvel, J., Le Calvez, S. & Ulfendahl, M. Image restoration for confocal microscopy: improving the limits of deconvolution, with application to the visualization of the mammalian hearing organ. *Biophysical journal* 80, 2455-2470 (2001).
15. Kohler, M., et al. On-line monitoring of apoptosis in insulin-secreting cells. *Diabetes* 52, 2943-2950 (2003).
16. Berney, T., et al. Endotoxin-mediated delayed islet graft function is associated with increased intra-islet cytokine production and islet cell apoptosis. *Transplantation* 71, 125-132 (2001).
17. Nyqvist, D., Köhler, M., Wahlstedt, H. & Berggren, P. O. Donor islet endothelial cells participate in formation of functional vessels within pancreatic islet grafts. *Diabetes* 54, 2287-2293 (2005).
18. Bernd, A. S., Aihara, M., Lindsey, J. D. & Weinreb, R. N. Influence of molecular weight on intracameral dextran movement to the posterior segment of the mouse eye. *Investigative ophthalmology & visual science* 45, 480-484 (2004).
19. Aynsley-Green, A., Biebuyck, J. F. & Alberti, K. G. Anaesthesia and insulin secretion: the effects of diethyl ether, halothane, pentobarbitone sodium and ketamine hydrochloride on intravenous glucose tolerance and insulin secretion in the rat. *Diabetologia* 9, 274-281 (1973).
20. Brown, E. T., Umino, Y., Loi, T., Solessio, E. & Barlow, R. Anesthesia can cause sustained hyperglycemia in C57/BL6J mice. *Visual neuroscience* 22, 615-618 (2005).
21. Desborough, J. P., Jones, P. M., Persaud, S. J., Landon, M. J. & Howell, S. L. Isoflurane inhibits insulin secretion from isolated rat pancreatic islets of Langerhans. *British journal of anaesthesia* 71, 873-876 (1993).

Troubleshooting

TABLE 1

| PROBLEM | POSSIBLE REASON | SOLUTION |
| --- | --- | --- |
| Movement of the graft during imaging (Step 12). | Movement of the head because the head holder is not properly fixed. | Fix the clamping of the head holder. |
| | Movement of the eye during normal breathing. | Adjust the eye stabilizer carefully. |
| | Gasping of the mouse. | Make sure that the airflow of the anesthesia unit and isofluorane levels are set properly. |
| No fluorescence can be detected in the blood vessels (Step 13 B ii). | Tail vein injection failed. | Repeat tail vein injection. |
| | Excitation and emission settings are wrong. | Adjust excitation and emission settings. |
| | Blood circulation to the eye is disrupted due to false setting of eye stabilizer. | Adjust the position of the eye stabilizer. |
| Perfusion does not work (Step 13 D x). | Air bubbles block the pipettes, capillary holder or tubing. | Make sure that there are no air bubbles in the tubing, capillary holders or capillaries, prior to the experiment. |
| | Dirt blocks the pipette tips. | Be sure to clean the pipettes after beveling, right before the experiment. |

We claim:

1. A method for treating a subject with type I diabetes, comprising transplanting onto the iris of the eye of a subject with type I diabetes, an amount effective of an isolated pancreatic islet or isolated pancreatic islet cell to promote insulin production in the subject.

2. The method of claim 1, wherein an isolated pancreatic islet is transplanted.

3. The method of claim 1, wherein an isolated pancreatic islet cell is transplanted.

4. The method of claim 1, wherein the transplantation onto the iris of the eye involves injection through the cornea.

5. The method of claim 4, wherein an isolated pancreatic islet is transplanted.

6. The method of claim 4, wherein an isolated pancreatic islet cell is transplanted.

* * * * *